United States Patent [19]

Tamai et al.

[11] 4,333,879

[45] Jun. 8, 1982

[54] EPOXYSUCCINIC ACID DERIVATIVES

[75] Inventors: Masaharu Tamai; Takashi Adachi; Shigeo Morimoto; Kiyoshi Oguma; Kazunori Hanada; Sadafumi Omura, all of Saitama, Japan

[73] Assignee: Taisho Pharmaceutical Co., Ltd., Tokyo, Japan

[21] Appl. No.: 109,410

[22] Filed: Jan. 3, 1980

[30] Foreign Application Priority Data

Feb. 27, 1979 [JP] Japan .................. 54/22365

[51] Int. Cl.³ .............. C07D 303/48; C07D 405/12; C07C 103/52
[52] U.S. Cl. ................ 549/549; 260/112.5 R; 546/207; 548/517
[58] Field of Search ............. 260/348.47, 326.36, 260/112.5 R; 546/207

[56] References Cited

U.S. PATENT DOCUMENTS 3,911,111 10/1975 Sawada et al. ............... 424/118
4,064,241 12/1977 Ross et al. .................. 424/246
4,091,221 5/1978 Carr et al. .................. 260/348.46

FOREIGN PATENT DOCUMENTS 2809036 9/1978 Fed. Rep. of Germany .

OTHER PUBLICATIONS

Chemical Abstracts, vol. 87 (1975) 68128z; 68129a; 85238c; 202108y; 202125b.
Hanada et al., Agric. Biol. Chem., vol. 42 (1978) No. 3, pp. 529-541.
T. Aoyagi et al., Jour. Antibiotics, vol. 22(6) (1969) pp. 283-286.
K. Maeda et al., Jour. Antibiotics, vol. 24(6) (1971) pp. 402-404.
S. Umezawa et al., Jour. Antibiotics, vol. 25(4) (1972) pp. 267-270.

Primary Examiner—Norma S. Milestone
Attorney, Agent, or Firm—Kenway & Jenney

[57] ABSTRACT

An epoxysuccinic acid derivative of the formula

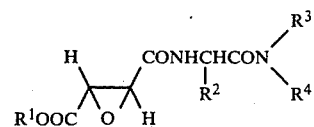

wherein $R^1$ is hydrogen, alkali metal, alkyl having 1-2 carbon atoms, cycloalkyl having 5-6 carbon atoms or benzyl, $R^2$ is alkyl having 3-4 carbon atoms or benzyl, $R^3$ is hydrogen or methyl, and $R^4$ is alkyl having 1-10 carbon atoms, phenyl, benzyl, phenethyl or cycloalkyl having 3-6 carbon atoms or $R^3$ and $R^4$ taken together with the nitrogen atom to which they are attached form a 5-6 membered heterocyclic ring, or said heterocyclic ring substituted with a protected carboxy.

3 Claims, No Drawings

EPOXYSUCCINIC ACID DERIVATIVES

BACKGROUND

The prior art discloses E-64 (U.S. Pat. No. 3,911,111), its intermediates [*Chemical Abstracts*, 87, 202108y (1977), ibid., 87, 85238c (1977), ibid., 87, 202125b (1977), ibid., 87, 68128z (1977)], and epoxysuccinic acid derivatives of German Patent Application Laying Open No. P 28 09 036 and *Chemical Abstracts*, 87, 68129a (1977) prepared by several of the present inventors.

The compounds of the present invention are distinguished from the prior art compounds by inhibitory activity to calcium-activated neutral thiolprotease (hereafter abbreviated as CANP) which exists in excess in muscle of muscular dystrophy mammals, and good absorption and by distribution in tissues after administration to mammals without acceleration of vascular permeability.

DESCRIPTION AND PREFERRED EMBODIMENTS

The present invention relates to a novel epoxysuccinic acid compound of the formula

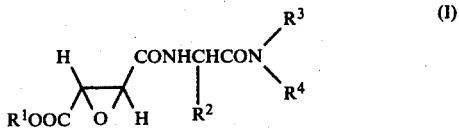

wherein
$R^1$ is hydrogen, alkali metal, alkyl having 1–2 carbon atoms, cycloalkyl having 5–6 carbon atoms or benzyl,
$R^2$ is alkyl having 3–4 carbon atoms or benzyl,
$R^3$ is hydrogen or methyl, and
$R^4$ is alkyl having 1–10 carbon atoms, phenyl, benzyl, phenethyl, cycloalkyl having 3–6 carbon atoms or a group of the formula

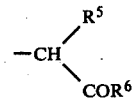

wherein
$R^5$ is hydrogen, alkyl having 1–4 carbon atoms or said alkyl substituted with hydroxy, methylmercapto, phenyl, hydroxyphenyl, indolyl, an optionally protected carboxy, an optionally protected amino or an optionally protected guanidino, and
$R^6$ is hydroxy, alkalimetaloxy, alkoxy having 1–2 carbon atoms, benzyloxy, amino or dimethylamino, or
$R^3$ and $R^4$ taken together with the nitrogen atom to which they are attached form a 5–6 membered heterocyclic ring, or said heterocyclic ring substituted with a protected carboxyl.

In the present specification and claims, unless otherwise noted, the term "alkyl" refers to both straight and branched chain alkyl groups, and the epoxysuccinic acid derivatives are trans isomers, namely, two carbonyl groups on the oxirane ring are in the trans configuration.

With regard to the compounds of the present invention, the protecting groups in the protected carboxy, amino and guanidino groups are conventionally protecting groups in the field of amino acid chemistry such as carbobenzoxy, methylbenzyloxycarbonyl, butoxycarbonyl, tosyl, benzyl, methyl, ethyl, acetyl, formyl, nitro and the like.

Preferred compounds of the present invention are the compounds of formula(I) wherein $R^1$ is hydrogen or alkali metal, $R^2$ is alkyl having 3–4 carbon atoms, $R^3$ is hydrogen, and $R^4$ is alkyl having 1–10 carbon atoms. More preferred compounds of the present invention are the compounds of formula(I) wherein $R^1$ is hydrogen, $R^2$ is alkyl having 4 carbon atoms, and $R^4$ is isoamyl.

A compound of formula(I) may be prepared, for example, as follows: An epoxysuccinic acid monoester of the formula

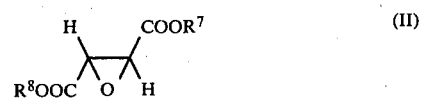

wherein
$R^7$ is hydrogen or alkali metal, and
$R^8$ is alkyl having 1–2 carbon atoms, cycloalkyl having 5–6 carbon atoms or benzyl, may be treated with a chlorinating agent such as oxalyl chloride, thionyl chloride or the like to give the corresponding acid chloride. To the acid chloride, an amino acid compounds of the formula

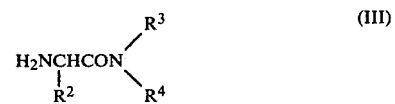

wherein $R^2$, $R^3$ and $R^4$ are as defined above, may be added dropwise under ice cooling to give the compound of formula(I) wherein $R^1$ is $R^8$. In this amidation, the amino acid compound may be accompanied by a base such as triethylamine, pyridine, methylmorphorine or the like. When the compound of formula(III) is employed directly in the form of an acid-addition salt, it may be provided for the reaction after removeing the acid with a base such as an alkali hydroxide, triethylamine, pyridine or methylmorpholine, alternatively it may be allowed to react in the presence of the base mentioned above.

The compound of formula(II) wherein $R^7$ is hydrogen also can be directly converted to the compound of formula(I) wherein $R^1$ is $R^8$ without chlorinating. In this case, the compound of formula(II) wherein $R^7$ is hydrogen may be reacted with the compound of formula(III) in the presence of a condensing agent such as N,N'-dicyclohexylcarbodiimide, 1-ethyl-3(3-dimethylaminopropyl)carbodiimide (hereinafter abbreviated as W.S.C.) or the like. Also preferred in this reaction is the addition of an N-hydroxy compound such as N-hydroxysuccinimide, 1-hydroxybenzotriazole or the like.

Alternatively, the compound of formula(I) wherein $R^1$ is $R^8$ may be prepared by the amidation of the compound of the formula

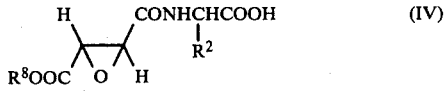

wherein R[2] and R[8] are as defined above, with an amine of the formula

wherein R[3] and R[4] are as defined above. This amidation can be carried out by following the same procedure as that of the reaction of the compound of formula(II) wherein R[7] is hydrogen with the compound of formula(III).

Also alternatively, the compound of formula(I) wherein R[1] is R[8] may be prepared by ester-exchange reaction of the compound of formula(I), wherein R[1] is another ester within the scope of R[8] with an alcohol, which can form the desired ester group of R[8], such as methanol, ethanol, cyclopentanol, cyclohexanol, or benzyl alcohol, in the presence of a catalyst such as sulfuric acid, an alkali metal alcoholate or an alkali hydroxide such as sodium hydroxide, potassium hydroxide or the like.

The compound of formula(I) wherein R[1] is alkali metal may be prepared by a process which comprises treating the compound of formula(I) wherein R[1] is R[8] with an alkali hydroxide such as sodium hydroxide, potassium hydroxide or the like, and then, if necessary, following by addition of an organic solvent such as ethanol, acetone, ethyl ether, petroleum ether or the like.

The compound of formula(I) wherein R[1] is hydrogen may be prepared by a process which comprises acidifying the compound of formula(I) wherein R[1] is alkali metal with an inorganic acid such as hydrochloric acid or sulfuric acid, or an organic acid such as formic acid or acetic acid, and then, extracting with a suitable organic solvent such as ethyl acetate, ethyl ether, benzene or chloroform.

In case where the compound of formula(I) has amino protected with carbobenzoxy, guanidino protected with nitro, or carboxy protected with benzyl, such protecting groups may be removed by catalytic reduction using palladium-on-charcoal or palladium black.

The compounds of formulae(II) and (IV) can be prepared by the method as described in German Patent Application Laying Open No. P 28 09 036 or by that with some modification.

The compound of formula(III) can be prepared as follows: The compound of the formula

wherein R[2] is as defined above and R[9] is a protecting group, may be reacted with the compound of formula(V), followed by removal of the protecting group to give the desired compound. Examples of the protecting group are conventional groups in the field of peptide synthesis such as t-butoxycarbonyl, carbobenzoxy or methylbenzyloxycarbonyl. The amidation of the compound of formula(VI) with the compound of formula(V) can be carried out by following the same procedure as that of the reaction of the compound of formula(II) wherein R[7] is hydrogen with the compound of formula(III). Removal of the protecting group can be carried out according to the conventional manner in the field of peptide chemistry.

The compounds of formulae(V) and (VI) are to a large extent commercially available.

The compounds of the present invention have superior inhibitory activity to CANP which exists in excess in muscle of muscular dystrophy mammals, and superior absorption and distribution in tissues after administration to mammals as compared with the epoxysuccinic acid derivatives of German Patent Application Laying Open No. P 28 09 036 and Chemical Abstracts, 87, 68129a (1977). Their muscular dystrophy inhibitory activity was assayed by the method of Ishiura et al, [J. of Biochem., 84, 225(1978)] using CANP prepared from a muscle of hereditary muscular dystrophy chicken, and the resulting value for 50% inhibition in the molar ratios for the enzyme expressed as $ID_{50}$ (mole/mole) is shown in Table 1.

The compounds of the present invention are better absorbed by the subcutaneous route in mammals such as rats or rabbits, as compared with the epoxysuccinic acid derivatives of the German Patent Laid Open Application described above and Chemical Abstracts, 87, 68129a (1977). To determine absorption, these compounds were administered subcutaneously to rat at a dose of 50 mg/kg, and the concentration of the test compound in rat plasma at an hour after the administration was shown in Table 1.

TABLE 1

| Compound | CANP Inhibitory Activity $ID_{50}$ (mole/mole) | Concentration in rat plasma (μg/ml) |
|---|---|---|
| 12 | 65 | 1.3 |
| 15 | 35 | 20 |
| 16 | 90 | 12 |
| 19 | 23 | 1.5 |
| 30 | 100 | 2.0 |
| 36 | 200 | 1.8 |
| 42 | 120 | 1.1 |
| 43 | 100 | 7.0 |
| 45 | 64 | 15 |
| A | 5,400 | below 1.0 |
| B | 410 | " |
| C | 580 | below 1.0 |
| D | 574 | " |
| E | 4,600 | " |

(Note)
Number in compound column of Table 1 means a compound which is prepared in the following Example attached the example number corresponding to said number. Also, symbols A–E in compound column of Table 1 mean the following known compounds:

A: Ethyl hydrogen epoxysuccinate
B: Benzyl hydrogen epoxysuccinate
C: N-(3-ethoxy-carbonyloxirane-2-carbonyl)-L-leucine benzyl ester
D: N-(3-carboxyoxirane-2-carbonyl)-L-phenylalanine benzyl ester
E: N-(3-carboxyoxirane-2-carbonyl)-L-leucine The compounds of the present invention also inhibit effectively and specifically thiol proteases such as papain, bromelains and some kinds of cathepsin in which some sulfhydryl groups are essential for activity. On the other hand, they have neither inhibitory activity against proteolysis of casein by trypsin, chymotrypsin, pepsin, an acid protease of Paecilomyces varioti or Nagase (trademark of Nagase Industry), against esteolysis of benzoylarginine ethyl ester by kallikrein nor against fibrinolysis by human plasmin.

Papain inhibitory activity of the compounds of the present invention was assayed by the method of K. Hanada et al, [Argric. Biol. Chem., 42, No. 3, 523(1978)] using papain (80 μg/ml, Sigma Chem. Co., 2×cry.). The amounts of inhibitor for 50% inhibition was expressed as $ID_{50}$ and shown in Table 2.

TABLE 2

| Compound | $ID_{50}$ (μg) | Compound | $ID_{50}$ (μg) | Compound | $ID_{50}$ (μg) |
|---|---|---|---|---|---|
| 1 | 0.439 | 10 | 0.510 | 19 | 0.123 |
| 2 | 0.227 | 11 | 0.184 | 20 | 0.255 |
| 3 | 1.10 | 12 | 0.260 | 21 | 0.169 |
| 4 | 0.417 | 13 | 0.255 | 22 | 8.28 |
| 5 | 0.284 | 14 | 0.187 | 23 | 0.221 |
| 6 | 0.410 | 15 | 0.112 | 24 | 0.219 |
| 7 | 0.410 | 16 | 0.123 | 25 | 0.223 |
| 8 | 0.446 | 17 | 0.255 | 26 | 0.139 |
| 9 | 0.313 | 18 | 29.07 | 27 | 0.216 |
| 28 | 0.156 | 35 | 0.212 | 42 | 0.595 |
| 29 | 0.35 | 36 | 0.595 | 43 | 0.195 |
| 30 | 0.391 | 37 | 2.50 | 44 | 0.250 |
| 31 | 0.375 | 38 | 0.305 | 45 | 0.236 |
| 32 | 0.227 | 39 | 0.408 | 46 | 0.105 |
| 33 | 0.255 | 40 | 0.481 | 47 | 0.260 |
| 34 | 0.298 | 41 | 0.272 | 48 | 0.215 |

(Note)
Number in compound column of Table 2 is as defined in Table 1.

The compounds of the present invention show no side-effect such as acceleration of vascular permeability and are superior to E-64 and its intermediates in this regard.

The pharmaceutical forms contemplated by the present invention include pharmaceutical compositions suited for oral, parenteral, and rectal use, e.g., tablets, powder packets, cachets, dragees, capsules, solutions, suspensions, sterile injectable forms, suppositories, bougies, and the like. The carrier employed may be, for example, either a solid or liquid. Examples of solid carriers are lactose, terra alba, sucrose, talc, gelatin, agar, pectin, acacia, magnesium stearate, stearic acid and the like. Examples of liquid carriers are syrup, peanut oil, olive oil, water and the like. Similarly, the carrier or diluent can include any time delay material well known to the art, such as glyceryl monostearate or glyceryl distearate alone or with a wax.

The compounds of the present invention can be used to inhibit CANP which exists in excess in muscle of muscular dytrophy mammals by the administration of about 5 to 400 mg/kg/day in single or two to four divided doses in oral or injectable preparations as described above.

The compounds of the present invention are of extremely low toxicity. That is, they show hardly any oral acute toxicity on mice at the dosages less than 2 g/day of body weight. Moreover, no side-effect is observed after administration of 1 g/kg/day orally for 30 days to laboratory animals.

The following examples show representative compounds encompassed within the scope of the present invention and the manner in which such compounds are prepared. However, it is to be understood that the examples are for purposes of illustration only.

EXAMPLE 1

In 30 ml of tetrahydrofuran were dissolved 1.09 g of N-(DL-3-trans-ethoxycarbonyloxirane-2-carbonyl)-L-leucine, 0.43 g of hexylamine, 0.60 g of 1-hydroxybenzotriazole and 0.44 g of N-methylmorpholine. To the solution was added little by little 0.84 g of W.S.C. hydrochloride under ice-cooling and stirring. The mixture was stirred for 2 hours keeping that temperature and another an hour at room temperature. The solution was concentrated and to the resulting residue were added 80 ml of water and 80 ml of ethyl acetate. The mixture was shaken and the ethyl acetate layer was separated. The aqueous layer was further extracted twice with ethyl acetate. The extracts were combined with the said ethyl acetate layer, washed successively with a 10% aqueous hydrochloric acid solution, a saturated sodium bicarbonate solution and a saturated sodium chloride solution, dried over magnesium sulfate and concentrated to dryness. The resulting residue was purified by silica gel column chromatography (chloroform:acetone=40:1) and crystallized from chloroform-ethyl ether to give 0.97 g of N-[N'-(DL-3-trans-ethoxycarbonyloxirane-2-carbonyl)-L-leucyl]cyclohexylamine, m.p. 168°–169° C.

EXAMPLE 2

Following the procedure of Example 1 and using 1.09 g of N-(DL-3-trans-ethoxycarbonyloxirane-2-carbonyl)-L-leucine and 0.69 g of n-decylamine, there was obtained 1.0 g of N-[N'-(DL-3-trans-ethoxycarbonyloxirane-2-carbonyl)-L-leucyl]-n-decylamine as viscous oil.

$IR\nu_{max}^{neat}$ (cm$^{-1}$): 3270 (amine), 1750 (ester), 1635, 1560 (amide), 897 (epoxy).

NMR (60 MHz, CDCl$_3$) δ=0.92 (d, J=5 Hz, 6H), 1.25 (b.s., 22H), 1.6 (b.s., 3H), 3.18 (m, 2H), 3.42 (d, J=2 Hz, 0.5H), 3.48 (d, J=2 Hz, 0.5H), 3.63 (d, J=2 Hz, 1H), 4.19 (q, J=7 Hz, 2H), 4.0–4.7 (m, 1H), 6.2–6.6 (br., 1H), 6.6–7.1 (br., 1H).

Mass m/e=412 (M+).

EXAMPLE 3

Following the procedure of Example 1 and using 1.09 g of N-(DL-3-trans-ethoxycarbonyloxirane-2-carbonyl)-L-leucine and 0.31 g of pyrrolidine, there was obtained 0.89 g of oily N-[N'-(DL-3-trans-ethoxycarbonyloxirane-2-carbonyl)-L-leucyl]pyrrolidine.

$IR\nu_{max}^{neat}$ (cm$^{-1}$): 3250 (amine), 1740 (ester, 1680, 1620, 1540 (amide), 895 (epoxy).

NMR (60 MHx, CDCl$_3$) δ=0.94 (d, J=5 Hz, 3H), 0.96 (d, J=5 Hz, 3H), 1.28 (t, J=7 Hz, 3H), 1.20–2.40 (m, 7H), 3.10–3.60 (m, 5H), 3.69 (d, J=2 Hz, 1H), 4.20 (q, J=7 Hz, 2H), 4.50–5.00 (m, 1H), 6.80–7.50 (br., 1H).

Mass m/e=326 (M+).

EXAMPLE 4

Following the procedure of Example 1 and using 1.09 g of N-(DL-3-trans-ethoxycarbonyloxirane-2-carbonyl)-L-leucine and 0.37 g of piperidine, there was obtained 0.7 g of oily N-[N'-(DL-3-trans-ethoxycarbonyloxirane-2-carbonyl)-L-leucyl]piperidine.

$IR\nu_{max}^{neat}$ (cm$^{-1}$): 3250 (amine), 1735 (ester), 1620, 1540 (amide), 895 (epoxy)

NMR (60 MHz, CDCl$_3$) δ=0.93 (t, J=5 Hz, 6H), 1.29 (t, J=7 Hz, 3H), 1.60 (b.s., 9H), 3.45 (b.s., 4H), 4.17 (q, J=7 Hz, 2H), 4.65–5.2 (m, 1H), 6.8–7.4 (br.; 1H)

Mess m/e=340 M+)

EXAMPLES 5–9

Following the procedure of Example 1 and using the corresponding starting materials, there were obtained the compounds of formula(I) in Table 3.

TABLE 3

$$\underset{R^1OOC}{H}\underset{O}{\diagdown}\underset{H}{\diagup}\overset{CONHCHCON}{\underset{R^2}{|}}\diagup\overset{R^3}{\diagdown R^4} \quad (I)$$

| Example | R¹ | R² | $-N\diagup^{R^3}_{\diagdown R^4}$ | m.p. (°C.) |
|---|---|---|---|---|
| 5 | CH₃CH₂— | $\underset{CH_3}{CH_3}\diagdown CHCH_2-$ | —NH—◁ | 148–149 |
| 6 | " | " | —NH—△(cyclobutyl) | 146.5–147.5 |
| 7 | " | " | —NHCH₂CH₂CH(CH₃)₂ | 108–110 |
| 8 | " | " | —NHCH₂CH₂—Ph | 131–132 |
| 9 | " | " | —NHCH₂CH₂CH₃ | 122–124 |

EXAMPLE 10

In 10 ml of tetrahydrofuran were dissolved 0.36 g of DL-trans-benzylhydrogenoxirane-2,3-dicarboxylate, 0.35 g of N-L-leucyl-N-methylaniline, 0.23 g of 1-hydroxybenzotriazole and 0.17 g of N-methylmorpholine. To the solution was added little by little 0.33 g of W.S.C. hydrochloride with ice-cooling and stirring. The mixture was stirred for 2 hours keeping that temperature and another an hour at room temperature. The solution was concentrated to distil off almost tetrahydrofuran and the resulting residue was suspended in 50 ml of water and extracted three times with 50 ml of ethyl acetate each. The extracts were combined, washed successively with a 5% aqueous hydrochloric acid solution, a saturated sodium bicarbonate solution and a saturated aqueous sodium chloride solution, dried and concentrated to dryness. The resulting oil was purified by silica gel column chromatography (chloroform:acetone=40:1) to give 0.57 g of oily N-[N'-(DL-3-trans-benzyloxycarbonyloxirane-2-carbonyl)-L-leucyl]-N-methylaniline.

IR$\nu_{max}^{neat}$ (cm⁻¹): 3265 (amine), 1753 (ester), 1650, 1530 (amide), 893 (epoxy).

NMR (60 MHz, CDCl₃) $\delta$=0.38 (d, J=5 Hz, 3H), 0.70 (d, J=5 Hz, 3H), 1.10–1.80 (m, 3H), 3.16 (d, J=2 Hz, 0.5H), 3.18 (s, 3H), 3.42 (d, J=2 Hz, 0.5H), 3.58 (d, J=2 Hz, 1H), 4.20–4.80 (m, 1H), 4.95 (s, 1H), 5.08 (s, 1H), 6.40–6.90 (br., 1H), 6.90–7.70 (m, 10H).

Mass m/e=424 (M+).

EXAMPLE 11

Following the procedure of Example 10 and using 1.4 g of DL-trans-benzylhydrogenoxirane-2,3-dicarboxylate and 0.99 g of N-L-leucyldimethylamine, there was obtained 1.68 g of oily N-[N'-(DL-3-trans-benzyloxycarbonyloxirane-2-carbonyl)-L-leucyl]dimethylamine.

IR$\nu_{max}^{neat}$ (cm⁻¹): 3260 (amine), 1753 (ester), 1690, 1630, 1540 (amide), 895 (epoxy).

NMR (60 MHz, CDCl₃) $\delta$=0.92 (d, J=5 Hz, 3H), 0.99 (d, J=5 Hz, 3H), 1.10–1.80 (m, 3H), 2.90 (s, 3H), 3.04 (s, 3H), 3.49 (d, J=2 Hz, 0.5H), 3.56 (d, J=2 Hz, 0.5H), 3.66 (d, 2 Hz, 1H), 4.70–5.00 (m, 1H), 5.14 (s, 2H), 6.50–7.10 (br., 1H), 7.27 (s, 5H).

Mass m/e=362 (M+).

EXAMPLE 12

Following the procedure of Example 10 and using 2.2 g of DL-trans-benzylhydrogenoxirane-2,3-dicarboxylate and 2.3 g of N-L-isoleucyl-N-methylbenzylamine, there was obtained 2.8 g of oily N-[N'-(DL-3-trans-benzyloxycarbonyloxirane-2-carbonyl)-L-isoleucyl]-N-methylbenzylamine.

IR$\nu_{max}^{neat}$ (cm⁻¹): 3255 (amine), 1750 (ester), 1685, 1630, 1535 (amide), 897 (epoxy).

NMR (60 MHz, CDCl₃). $\delta$=0.89 (b.s., 6H), 1.0–2.0 (m, 3H), 2.95 (s, 3H), 3.47 (d, =J=2 Hz, 0.5H), 3.52 (d, J=2 Hz, 0.5H), 3.68 (d, J=2 Hz, 1H), 4.1–4.95 (m, 3H), 5.10 (s, 2H), 6.5–7.4 (m, 11H).

Mass m/e=438 (M+).

EXAMPLE 13

0.2 g of N-[N'-(DL-3-trans-ethoxycarbonyloxirane-2-carbonyl)-L-leucyl]cyclohexylamine was dissolved in a mixture of 1 ml of cyclohexylalcohol and 5 ml of benzene. After adding one drop of conc. sulfuric acid, the solution was refluxed for 15 hours. After reflux, 50 ml of benzene was added to the solution. The mixture was washed successively with a saturated aqueous sodium bicarbonate solution and a saturated aqueous sodium chloride solution and concentrated to dryness. The resulting residue was purified by silica gel column chromatography (chloroform:acetone=70:1) and crystallized from chloroform-ethyl ether to give 0.16 g of N-[N'-(DL-3-trans-cyclohexyloxycarbonyloxirane-2-carbonyl)-L-leucyl]cyclohexylamine, m.p. 185.5°–186.5° C.

EXAMPLE 14

Following the procedure of Example 13 and using 0.2 g of N-[N'-(DL-3-trans-ethoxycarbonyloxirane-2-carbonyl)-L-leucyl]cyclopentylamine and 1 ml of cyclopentylalcohol, there was obtained 0.15 g of N-[N'-

(DL-3-trans-cyclopentyloxycarbonyl)-L-leucyl]cyclopentylamine, m.p. 158°–160° C.

EXAMPLE 15

0.34 g of N-[N'-(DL-3-trans-ethoxycarbonyloxirane-2-carbonyl)-L-leucyl]isopropylamine was dissolved in 5 ml of ethanol, followed by adding 0.056 g of potassium hydroxide in 2 ml of ethanol under ice-cooling and stirring. The mixture was stirred for 2 hours under ice-cooling. To the mixture was added 50 ml of ethyl ether and the produced precipitates were collected by filtration to afford 0.23 g of N-[N'-(DL-3-trans-carboxyoxirane-2-carbonyl)-L-leucyl]isopropylamine potassium salt, m.p. 174°–175° C. (with decomposition).

EXAMPLE 16

Following the procedure of Example 15 and using 0.37 g of N-[N'-(DL-3-trans-ethoxycarbonyloxirane-2-carbonyl)-L-leucyl]phenethylamine and 0.056 g of potassium hydroxide, there was obtained 0.23 g of N-[N'-(DL-3-trans-carboxyoxirane-2-carbonyl)-L-leucyl]-phenethylamine potassium salt, m.p. 163°–165° C. (with decomposition).

EXAMPLE 17

To 30 ml of a benzene solution containing 1.5 g of L-leucyl-L-leucine benzyl ester and 0.55 g of triethylamine was added dropwise 20 ml of a benzene solution containing 1.2 g of epoxysuccinic acid monobenzyl ester chloride over 30 minutes under ice-cooling and stirring. The mixture was stirred for 2 hours under ice-cooling and another an hour at room temperature. The produced precipitates were filtered off. The resulting filtrate was washed successively with a 5% aqueous hydrochloric acid solution, a saturated sodium bicarbonate solution and a saturated aqueous sodium chloride solution, dried over magnesium sulfate and concentrated to dryness. The resulting residue was purified by silica gel column chromatography (ethyl acetate:n-hexane=1:2) and crystallized from ethyl ether-petroleum ether to give 1.8 g of N-(DL-3-trans-benzyloxycarbonyloxirane-2-carbonyl)-L-leucyl-L-leucine benzyl ester, m.p. 91°–93° C.

EXAMPLE 18

Following the procedure of Example 17 and using 0.46 g of L-phenylalanyl-L-phenylalanine methyl ester and 0.26 g of epoxysuccinic acid monoethyl ester chloride, there was obtained 0.27 g of N-(DL-3-trans-ethoxycarbonyloxirane-2-carbonyl-L-phenylalanyl-L-phenylalanine methyl ester, m.p. 142°–143° C.

EXAMPLE 19

Following the procedure of Example 17 and using 1.3 g of L-leucyl-L-proline methyl ester and 1.4 g of epoxysuccinic acid monobenzyl ester chloride, there was obtained 1.32 g of oily N-(DL-3-trans-benzyloxycarbonyloxirane-2-carbonyl)-L-leucyl-L-proline methyl ester.

IR$_{max}^{neat}$ (cm$^{-1}$): 3300 (amine), 1750 (ester), 1690, 1630, 1550 (amide), 900 (epoxy).

NMR (60 MHz, CDCl$_3$) $\delta$=0.96 (d, J=5 Hz, 6H), 1.10–2.40 (m, 7H), 3.30–3.90 (m, 4H), 3.64 (s3H), 4.10–4.90 (m, 2H), 5.11 (s, 2H), 6.30–7.00 (br., 1H), 7.27 (s, 5H).

Mass m/e=446 (M+).

EXAMPLE 20

To a solution of 1.5 g of DL-trans-benzylhydrogenoxirane-2,3-dicarboxylate, 1.75 g of L-leucine-L-glutamic acid dimethyl ester, 0.88 g of 1-hydroxybenzotriazole and 0.66 g of N-methylmorpholine in 50 ml of tetrahydrofuran was added little by little 1.24 g of W.S.C. hydrochloride under ice-cooling and stirring. The mixture was stirred for an hour under ice-cooling and for another 2 hours at room temperature. Tetrahydrofuran was almost distilled off under reduced pressure. 80 ml of water was added to the resulting residue and the mixture was extracted twice with 80 ml of ethyl acetate each. The ethyl acetate extracts were combined, washed successively with a 5% aqueous hydrochloric acid solution, a saturated sodium bicarbonate solution and a saturated aqueous sodium chloride, dried over magnesium sulfate and concentrated to dryness. The resulting residue was purified by silica gel column chromatography (chloroform:acetone=70:1) and crystallized from chloromethyl ether to give 1.65 g of N-(DL-3-trans-benzyloxycarbonyloxirane-2-carbonyl)-L-leucyl-L-gluamic acid dimethyl ester, m.p. 126°–128° C.

EXAMPLE 21

Following the procedure of Example 20 and using 1.3 g of DL-trans-benzylhydrogenoxirane-2,3-dicarboxylate and 1.3 g of L-leucyl-L-isoleucine methyl ester, there was obtained 2.2 g of oily N-(DL-3 trans-benzyloxycarbonyloxirane-2-carbonyl)L-leucyl-L-isoleucine methyl ester.

IR$\nu_{max}^{neat}$ (cm$^{-1}$): 3300 (amine), 1740 (ester), 1660, 1550 (amide), 900 (epoxy).

NMR (60 MHz, CDCl$_3$) $\delta$=0.92 (b.s., 12H), 1.3–2.0 (m, 6H), 3.45 (d, J=2 Hz, 0.5H), 3.49 (d, J=2 Hz, 0.5H), 3.63 (d, J=2 Hz, 1H), 3.66 (s, 3H), 4.2–4.7 (m, 2H), 5.13 (s, 2H), 6.3–6.7 (br., 2H), 7.26 (s, 5H).

Mass m/e=462 (M+)

EXAMPLE 22

Following the procedure of Example 20 and using 0.96 g of DL-trans-benzylhydrogenoxirane-2,3-dicarboxylate and 1.12 g of D-leucyl-L-leucine methyl ester, there was obtained 1.3 g of N-(DL-3-trans-benzyloxycarbonyloxirane-2-carbonyl)-D-leucyl-L-leucine methyl ester as viscous oil.

IR$\nu_{max}^{neat}$ (cm$^{-1}$): 3260 (amine), 1740 (ester), 1670, 1645, 1553 (amide), 897 (epoxy).

NMR (60 MHz, CDCl$_3$) $\delta$=0.91 (d, J=5 Hz, 12H), 1.2–2.0 (m, 6H), 3.46 (d, J=2 Hz, 0.5H), 3.59 (s, 3H), 3.60 (d, J=2 Hz, 0.5H), 3.66 (d, J=2 Hz, 1H), 4.20–4.90 (m, 2H), 5.12 (s, 2H), 6.30–6.70 (br., 2H), 7.24 (s, 5H).

Mass m/e=462 (M+).

EXAMPLE 23

Following the procedure of Example 20 and using 0.95 g of DL-trans-benzylhydrogenoxirane-2,3-dicarboxylate and 1.1 g of L-leucyl-D-leucine methyl ester, there was obtained 1.38 g of N-(DL-3-trans-benzyloxycarbonyloxirane-2-carbonyl)-L-leucyl-D-leucine methyl ester as viscous oil.

IR$\nu_{max}^{neat}$ (cm$^{-1}$): 3270 (amine), 1740 (ester), 1670, 1645, 1545 (amide), 895 (epoxy).

NMR (60 MHz, CDCl$_3$) $\delta$=0.90 (d, J=5 Hz, 6H), 1.30–1.90 (m, 3H), 3.45 (d, J=2 Hz, 0.5H), 3.55–3.70 (m, 1.5H), 3.62 (s, 3H), 4.10–4.80 (m, 2H), 5.12 (s, 2H), 6.30–6.70 (br., 2H), 7.22 (s, 5H).

Mass m/e=462 (M+).

EXAMPLE 24

0.5 g of N-(DL-3-trans-benzyloxycarbonyloxirane-2-carbonyl)-L-leucyl-D-leucine methyl ester obtained in Example 23 was adsorbed by cilica gel column chromatography (1.5 cm×40 cm, chloroform). 5 g of the silica gel was placed in each test tube and treated with thin layer chromatography (silica gel, chloroform:acetone=40:1) to obtain two fractions, one of which contained the compound having higher Rf value and the other contained the compound having lower Rf value.

The fraction containing the compound having higher Rf value was concentrated and the resulting residue was crystallized from ethyl ether-petroleum ether to obtain 0.15 g of N-(D-3-trans-benzyloxycarbonyloxirane-2-carbonyl)-L-leucyl-D-leucine methyl ester, m.p. 95°–97° C., $[\alpha]_D^{28} = -51.1$ (c=1, ethanol).

EXAMPLE 25

The fraction containing the compound having lower Rf value, which was obtained from the silica gel in Example 24, was concentrated and the resulting residue was crystallized from ethyl ether-petroleum ether to give 0.14 g of N-(L-3-trans-benzyloxycarbonyloxirane-2-carbonyl)-L-leucyl-D-leucine methyl ester, m.p. 72°–73° C., $[\alpha]_D^{28} = +44.0$ (c=1, ethanol).

EXAMPLES 26–42

Following the procedure of Example 20 and using the corresponding starting materials, there were obtained the compounds of formula (I) in Table 4.

TABLE 4

Structure (I):

$$R^1OOC-\underset{O}{\overset{H}{\triangle}}-CONHCHCON\underset{R^4}{\overset{R^3}{\diagup}}$$
(with $R^2$ on the CHCON carbon)

| Example | $R^1$ | $R^2$ | $-N\underset{R^4}{\overset{R^3}{\diagup}}$ | m.p. (°C.) |
|---|---|---|---|---|
| 26 | C$_6$H$_5$–CH$_2$– | CH$_3$\CHCH$_2$–/CH$_3$ | –Arg(NO$_2$)–OCH$_3$ | 184~185 |
| 27 | " | " | –Met–OCH$_3$ | 141~142 |
| 28 | CH$_3$– | " | " | 130~132 |
| 29 | C$_6$H$_5$–CH$_2$– | " | –Thr–OCH$_3$ | 102~103 |
| 30 | " | " | –Orn(z)–OCH$_2$–C$_6$H$_5$ | 146~149 |
| 31 | " | " | –Phe–OCH$_2$H$_5$ | 118~120 |
| 32 | " | " | –Leu–OCH$_3$ | 120~122 |
| 33 | " | " (D-isomer) | –Leu–OCH$_3$ (D-isomer) | 106~108 |
| 34 | " | " | –Leu–NH$_2$ | 186~187 |
| 35 | C$_2$H$_5$– | " | –Leu–N(CH$_3$)$_2$ | 109.5~110.5 |
| 36 | C$_6$H$_5$–CH$_2$– | C$_6$H$_5$–CH$_2$– | –Leu–OCH$_3$ | 147~148 |
| 37 | " | " | –Phe–OCH$_3$ | 113~114 |
| 38 | " | CH$_3$\CH–/C$_2$H$_5$ | –Trp–OCH$_3$ | 173~175 |
| 39 | C$_6$H$_5$–CH$_2$– | CH$_3$\CH–/C$_2$H$_5$ | –Tyr–OCH$_3$ | 113~115 |
| 40 | " | " | –Gly–OC$_2$H$_5$ | 167.5~168.5 |
| 41 | " | " | –Val–OCH$_3$ | 153~154 |
| 42 | " | CH$_3$\CH–/CH$_3$ | –Ala–OCH$_3$ | 192~195 |

(Note)
In the above Table Arg(NO$_2$) means N$^G$-nitro-L-arginyl group, Met methionyl group, Thr threonyl group, Orn(z) δ-carbobenzoxy-L-ornithyl group, Phe phenylalanyl group, Leu Leucyl group, Trp trypsinyl group, Tyr tyroxinyl group, Gly glycyl group, Val valyl group, Ala alanyl group, respectively and the compounds other than those described as D-isomer are L-isomer.

EXAMPLE 43

In a mixture of 8 ml of methanol, 2 ml of acetic acid and 1 ml of water was dissolved 0.1 g of N-(DL-3-trans-benzyloxycarbonyloxirane-2-carbonyl)-L-leucyl-N$^G$-nitro-L-arginine methyl ester obtained in Example 26. After addition of 50 mg of 5% palladium-on-charcoal, the mixture was stirred for 4 hours at room temperature in a weak stream of hydrogen. The reaction mixture was filtered and the filtrate was concentrated. The resulting residue was treated by column chromatography on Sephadex-LH20 (methanol) and crystallized from methanol-chloroform to obtain 0.068 g of N-(DL-3-trans-carboxyoxirane-2-carbonyl)-L-leucyl-L-arginine methyl ester, m.p. 160°–165° C. (with decomposition).

EXAMPLE 44

Following the procedure of Example 43 and using 0.31 g of N-(DL-3-trans-benzyloxycarbonyloxirane-2-carbonyl)-L-leucyl-δ-carbobenzoxy-L-ornithine benzyl ester obtained in Example 30 and crystalling the resulting product from water-acetone, there was obtained 0.1 g of N-(DL-3-trans-carboxyoxirane-2-carbonyl)-L-leucyl-L-ornithine, m.p. 187°–188° C.

EXAMPLE 45

In 20 ml of ethanol was dissolved 0.5 g of N-(DL-3-trans-benzyloxycarbonyloxirane-2-carbonyl)-L-leucyl-L-leucine benzyl ester obtained in Example 17. After addition of 0.2 g of 5% palladium-one-charcoal, the mixture was stirred for 6 hours at room temperature in a weak stream of hydrogen. The reaction mixture was filtered and the filtrate was concentrated. The resulting residue was crystallized from ethanol-ethyl ether to afford 0.32 g of N-(DL-3-trans-carboxyoxirane-2-carbonyl)-L-leucyl-L-leucine, m.p. 121°–123° C.

EXAMPLE 46

Following the procedure of Example 45 and using 0.21 g of N-(DL-3-trans-benzyloxycarbonyloxirane-2-carbonyl)-L-leucyl-L-proline methyl ester obtained in Example 19 and purifying the resulting concentrate by silica gel column chromatography (chloroform:methanol=20:1), there was obtained 0.095 g of oily N-(DL-3-trans-carboxyoxirane-2-carbonyl)-L-leucyl-L-proline methyl ester.

IR$\nu_{max}^{neat}$ (cm$^{-1}$): 3250 (amine), 1740 (ester), 1620, 1560 (amide), 900 (epoxy).

NMR (60 MHz, CDCl$_3$) δ=0.96 (d, J=5 Hz, 6H), 1.20–2.60 (m, 7H), 3.40–3.90 (m, 4H), 3.68 (s, 3H), 4.10–5.00 (m, 2H), 7.60–8.00 (br., 1H), 8.80–9.30 (br., 1H).

EXAMPLE 47

Following the procedure of Example 46 and using 0.188 g of N-(DL-3-trans-benzyloxycarbonyloxirane-2-carbonyl)-L-leucyl-L-glutamic acid dimethyl ester obtained in Example 20, there was obtained 0.1 g. of oily N-(DL-3-trans-carboxyoxirane-2-carbonyl)-L-leucyl-L-glutamic acid dimethyl ester.

IR$\nu_{max}^{neat}$ (cm$^{-1}$): 3280 (amine), 1730 (ester), 1650, 1550 (amide), 900 (epoxy).

NMR (60 MHz, CDCl$_3$) δ=0.92 (d, J=5 Hz, 6H), 1.20–2.70 (m, 7H), 3.57 (s, 3H), 3.63 (s, 3H), 3.45–3.70 (m, 2H), 4.10–4.80 (m, 2H), 5.90–6.50 (m, 2H), 7.10–7.70 (br., 1H)

EXAMPLE 48

In benzyl alcohol was dissolved 0.54 g of N-(DL-3-trans-benzyloxycarbonyloxirane-2-carbonyl)-L-leucyl-L-leucine benzyl ester obtained in Example 17. To the solution was added dropwise 5 ml of a benzyl alcohol solution containing 0.56 g of potassium hydroxide under ice-cooling and stirring. The mixture was stirred for 2 hours under ice-cooling. Petroleum ether was added to the reaction mixture and the produced precipitates were collected on a filter. They were dissolved in 10 ml of a 5% aqueous hydrochloric acid solution and extracted twice with 10 ml of ethyl acetate each. The extracts were combined, washed with a saturated sodium chloride solution and concentrated. The resulting residue was purified by silica gel column chromatography (chloroform:methanol=4:1) and crystallized from chloroform-n-hexane to obtain 0.23 g of N-(DL-3-trans-carboxyoxirane-2-carbonyl)-L-leucyl-L-leucine benzyl ester, m.p. 103°–104° C.

What is claimed is:

1. An epoxysuccinic acid derivative of the formula

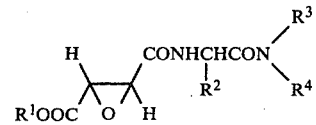

wherein
R$^1$ is hydrogen, alkali metal, alkyl having 1–2 carbon atoms, cycloalkyl having 5–6 carbon atoms or benzyl,
R$^2$ is a branched chain alkyl group having 3–4 carbon atoms or benzyl,
R$^3$ is hydrogen or methyl, and
R$^4$ is alkyl having 1–10 carbon atoms, phenyl benzyl, phenethyl, or cycloalkyl having 3–6 carbon atoms, or
R$^3$ and R$^4$ taken together with the nitrogen atom to which they are attached form a pyrrolidino heterocyclic ring, or said heterocyclic ring substituted with a protected carboxy.

2. A compound according to claim 1 wherein R$^1$ is hydrogen or alkali metal, R$^2$ is a branched chain alkyl group having 3–4 carbon atoms, R$^3$ is hydrogen and R$^4$ is alkyl having 1–10 carbon atoms.

3. A compound according to claim 2 wherein R$^1$ is hydrogen, R$^2$ is a branched chain alkyl group having 4 carbon atoms, R$^3$ is hydrogen and R$^4$ is isoamyl.

* * * * *